United States Patent [19]

Fischer et al.

[11] 4,335,118
[45] Jun. 15, 1982

[54] INSECTICIDAL α-CYANO-3-PHENOXY-BENZYL-2-(4-AZIDOPHENYL)-3-METHYLBUTYRATES

[75] Inventors: Hanspeter Fischer, Bottmingen; Rudolph C. Thummel, Courgenay; Rudolf Wehrli, Rheinfelden, all of Switzerland

[73] Assignee: Ciba-Geigy Corporation, Ardsley, N.Y.

[21] Appl. No.: 195,712

[22] Filed: Oct. 9, 1980

[30] Foreign Application Priority Data

Oct. 17, 1979 [CH] Switzerland ............ 9335/79
Jun. 4, 1980 [CH] Switzerland ............ 4332/80

[51] Int. Cl.³ .............. A01N 47/08; C07C 69/76; C07C 121/86
[52] U.S. Cl. .............. 424/226; 560/105; 260/349
[58] Field of Search .......... 560/105; 424/226; 260/349

[56] References Cited

U.S. PATENT DOCUMENTS 2,633,470 3/1953 Sullivan et al. .......... 260/349
4,045,575 8/1977 Searle et al. ............ 560/105
4,062,968 12/1977 Fujimoto et al. ......... 560/105

OTHER PUBLICATIONS

Abbanat et al., Chem. Abstracts, vol. 62, cols. 7023-7024, (1965), (note section 1 on azide).

*Primary Examiner*—Henry R. Jiles
*Assistant Examiner*—Robert C. Whittenbaugh
*Attorney, Agent, or Firm*—Frederick H. Rabin; John P. Spitals

[57] ABSTRACT

Phenylacetates of the formula

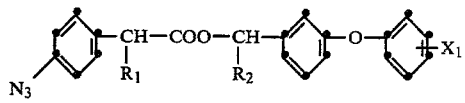

wherein $R_1$ is isopropyl or cyclopropyl, $R_2$ is hydrogen, cyano, ethynyl, prop-1-ynyl or —$CSNH_2$, and $X_1$ is hydrogen, methyl, fluorine or chlorine, a process for their production and method of use thereof in pest control.

5 Claims, No Drawings

INSECTICIDAL α-CYANO-3-PHENOXY-BENZYL-2-(4-AZIDO-PHENYL)-3-METHYLBUTYRATES

The present invention relates to α-phenylacetates, to the production thereof and method of use thereof in pest control.

The phenylacetates have the formula

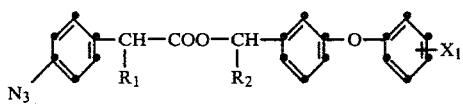
(I)

wherein $R_1$ is isopropyl or cyclopropyl, $R_2$ is hydrogen, cyano, ethynyl, prop-1-ynyl or —CSNH$_2$, and $X_1$ is hydrogen, methyl, fluorine or chlorine.

On account of their action, especially preferred compounds of the formula I are those wherein $R_1$ is isopropyl or cyclopropyl, $R_2$ is hydrogen, cyano, ethynyl, prop-1-ynyl or —CSNH$_2$, and $X_1$ is hydrogen p-fluorine or p-chlorine.

The most preferred compounds of the formula I, however, are those wherein $R_1$ is isopropyl, $R_2$ is cyano and $X_1$ is hydrogen, p-fluorine or p-chlorine.

The compounds of the formula I are obtained by methods which are known per se, e.g. as follows:

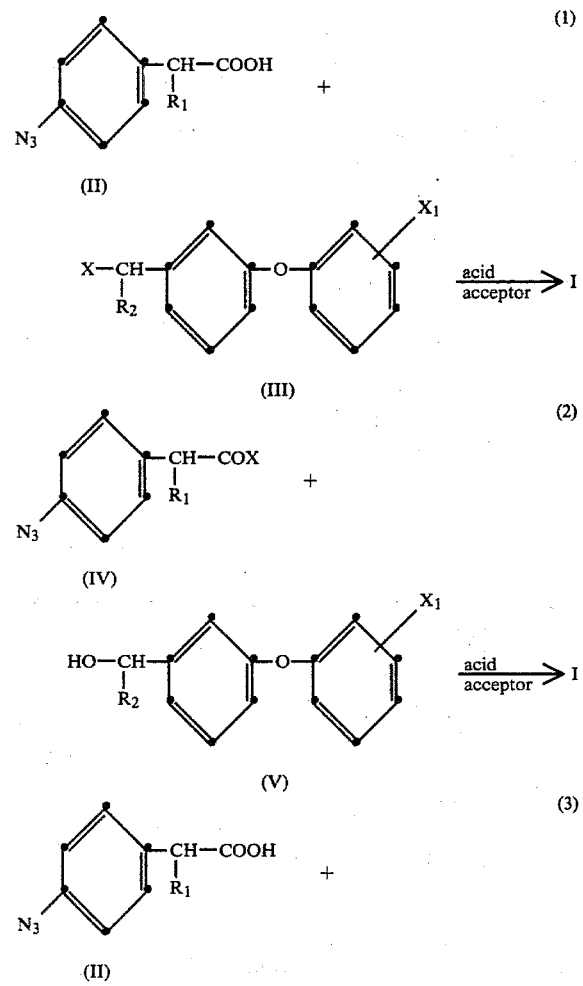

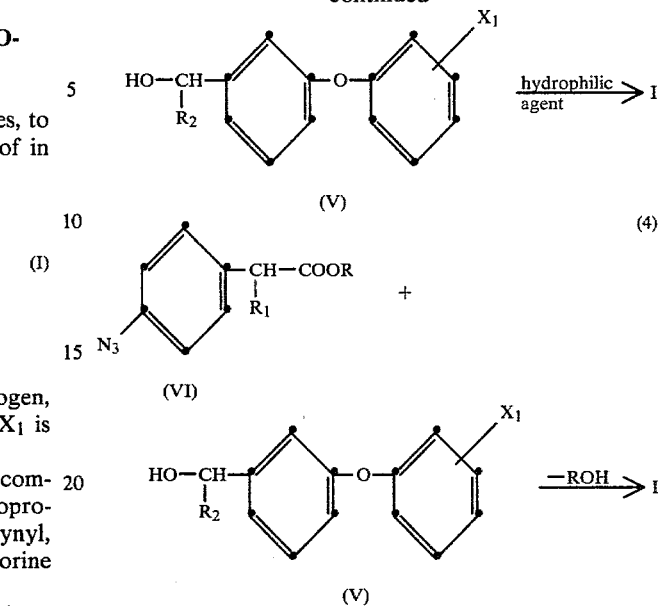

In the formulae II to VI above, $R_1$, $R_2$ and $X_1$ are as defined for formula I.

In formulae II and IV, X is a halogen atom, especially a chlorine or bromine atom, and in formula VI R is $C_1$–$C_4$alkyl, especially methyl or ethyl.

Suitable acid acceptors for processes 1 and 2 are, in particular, tertiary amines such as trialkylamine and pyridine, and also hydroxides, oxides, carbonates and bicarbonates of alkali metals and alkaline earth metals, as well as alkali metal alcoholates, for example potassium tert-butylate and sodium methylate. A suitable hydrophilic agent for process 3 is, for example, dicyclohexylcarbodiimide. Processes 1 to 4 are carried out at a reaction temperature in the range from −10° to 120° C., usually from 20° to 80° C., under normal or elevated pressure, and preferably in an inert solvent or diluent. Examples of suitable solvents or diluents are: ether and ethereal compounds, for example diethyl ether, diisopropyl ether, dioxane, dimethoxyethane and tetrahydrofurane; amides such as N,N-dialkylated carboxamides; aliphatic, aromatic and halogenated hydrocarbons, especially benzene, toluene, xylenes, chloroform and chlorobenzene; nitriles such as acetonitrile; dimethyl sulfoxide; and ketones such as acetone and methyl ethyl ketone.

The starting materials of the formulae III and V are known, whereas those of the formulae II, IV and VI are new. However, all starting materials can be obtained by known methods.

The compounds of the formula I exist in the form of a mixture of different optically active isomers if inhomogeneous optically active starting materials are used in the reaction. The different mixtures of isomers can be separated into the individual isomers by known methods. The compound of the formula I is to be understood as comprising both the individual isomers and the mixtures thereof. The compounds of the formula I are suitable for controlling a variety of pests of animals and plants. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

In particular, the compounds of the formula I are suitable for controlling plant destructive insects, especially plant-destructive feeding insects in ornamentals and crops of useful plants, especially in cotton plantations (e.g. *Spodoptera littoralis* and *Heliothis virescens*) and in vegetable crops (for example *Leptinotarsa decemlineata* and *Myzus persicae*).

The compounds of the formula I also have a very good action against flies, for example *Musca domestica*, and mosquito larvae.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyethroids, carbamates, and chlorinated hydrocarbons.

Compounds of the formula I are also combined with particular advantage with substances which exert a synergistic or potentiating effect on pyrethroids. Examples of such compounds include: piperonyl butoxide, propynyl ethers, propynyl oximes, propynyl carbamates and propynyl phosphates, 2-(3,4-methylenedioxyphenoxy)-3,6,9-trioxaundecane (Sexamex or Sesoxane), S,S,S-tributylphosphorotrithioate, 1,2-methylenedioxy-4(2-(octylsulfinyl)-propyl)-benzene.

The compounds of the formula I may be used by themselves alone or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

The compositions of the present invention are manufactured in known manner by homogeneously mixing and/or grinding compounds of the formula I with the appropriate carriers, if desired with the addition of dispersants or solvents which are inert to the active ingredients.

The compounds of the formula I may be processed to the following formulations:

Solid formulations:

Dusts, tracking powders and granules (coated granules, impregnated granules and homogeneous granules).

Liquid formulations:

(a) active ingredients which are dispersable in water: wettable powders, pastes and emulsions;

(b) solutions.

The content of active ingredient in the above described compositions is generally between 0.1% and 95%, though concentrations of up to 99.5% or even pure active ingredient can also be used if the compositions are applied from an aircraft or other appropriate application devices.

The compounds (active ingredients) of the formula I can, for example, be formulated as follows (throughout the present specification all parts and percentages are by weight):

Dusts: The following substances are used to formulate (a) a 5% and (b) a 2% dust:

(a)

5 parts of active ingredient,
95 parts of talc;

(b)

2 parts of active ingredient,
1 part of highly disperse silicic acid,
97 parts of talc.

The active ingredient is mixed with the carriers and ground.

Granules: The following substances are used to formulate 5% granules:

5 parts of active ingredient,
0.25 parts of epoxidised vegetable oil,
0.25 parts of cetyl polyglycol ether,
3.50 parts of polyethylene glycol,
91 parts of kaolin (particle size 0.3–0.8 mm).

The active ingredient is mixed with the epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable powders: The following constituents are used to formulate (a) a 40%, (b) and (c) a 25%, and (d) a 10% wettable powder:

(a)

40 parts of active ingredient,
5 parts of sodium lignosulfonate,
1 part of sodium dibutylnaphthalenesulfonate,
54 parts of silicic acid;

(b)

25 parts of active ingredient,
4.5 parts of calcium lignosulfonate,
1.9 parts of Champagne chalk/hydroxyethyl cellulose mixture (1:1),
1.5 parts of sodium dibutylnaphthalenesulfonate,
19.5 parts of silicic acid,
19.5 parts of Champagne chalk,
28.1 parts of kaolin;

(c)

25 parts of active ingredient,
2.5 parts of isooctylphenoxy-polyoxyethylene ethanol,
1.7 parts of Champagne chalk/hydroxyethyl cellulose mixture (1:1),
8.3 parts of sodium aluminum silicate,
16.5 parts of kieselgur,
46 parts of kaolin;

(d)

10 parts of active ingredient,
3 parts of a mixture of the sodium salts of saturated fatty alcohol sulfates,
5 parts of naphthalenesulfonic acid/formaldehyde condensate,
82 parts of kaolin.

The active ingredient is homogeneously mixed with the adjuvants in suitable mixers and the mixture is then ground in appropriate mills and rollers. The resultant wettable powders can be diluted with water to give suspensions of any desired concentration.

Emulsifiable concentrates: The following substances are used to formulate (a) a 10%, (b) a 25% and (c) a 50% emulsifiable concentrate:

(a)

10 parts of active ingredient,
3.4 parts of epoxidised vegetable oil, 3.4 parts of a combination emulsifier consisting of a fatty alcohol polyglycol ether and calcium alkylarylsulfonate,
40 parts of dimethyl formamide,
43.2 parts of xylene;

(b)

25 parts of active ingredient,
2.5 parts of epoxidised vegetable oil,
10 parts of alkylarylsulfonate/fatty alcohol polyglycol ether mixture,
5 parts of dimethyl formamide,
57.5 parts of xylene;

(c)

50 parts of active ingredient,
4.2 parts of tributylphenol polyglycol ether,
5.8 parts of calcium dodecylbenzenesulfonate,
20 parts of cyclohexanone,
20 parts of xylene.

By diluting these concentrates with water it is possible to obtain emulsions of any required concentration.

Sprays: The following ingredients are used to formulate (a) a 5% spray, and (b) a 95% spray:

(a)

5 parts of active ingredient,
1 part of epoxidised vegetable oil
94 parts of white spirit (boiling range 160°–190° C.);

(b)

95 parts of active ingredient,
5 parts of epoxidised vegetable oil.

The invention is further illustrated by the following Examples.

EXAMPLE 1

Production of (±)-α-cyano-3-phenoxybenzyl (−)-2-(4-azidophenyl)-3-methylbutyrate (a) (−)-2(4-Azidophenyl)-3-methylbutyric acid A solution of 65.7 g of (±)-2(4-azidophenyl)-3-methylbutyric acid in 800 ml of 63% ethanol is heated to 60° C. and stirred into a solution of 36.3 g of (±)-phenylethylamine in 560 ml of 63% ethanol at 60° C. The solution obtained is cooled to room temperature in the course of 12 hours and the crystallised salt (43 g) is collected by filtration and recrystallised twice from 63% ethanol, affording 12.5 g of salt from which the desired acid can be isolated by treatment with dilute hydrochloric acid, extraction with ethyl acetate, drying the organic phase over Na$_2$SO$_4$, and concentrating the residue. Two recrystallisations from hexane yield the pure (−)-2(4)-azidophenyl)-3-methylbutyric acid with a melting point of 95°–97° C. and a specific rotation $[\alpha]_D^{20°}$ of −48° (CHCl$_3$, c=0.75). Further recrystallisation of the salt did not alter the rotation of the acid obtained therefrom.

(b) (−)-2(4-Azidophenyl)-3-methylbutyryl chloride 1.5 g of the acid obtained in (a) and 1.3 g of oxalyl chloride are heated to 60° C. in 35 ml of hexane. Then 1 drop of dimethyl formamide is added and the mixture is stirred for 1 hour at 60° C. The cold solution is decanted and evaporated in a rotary evaporator. The resultant (−)-2(4-azidophenyl)-3-methylbutyryl chloride is further processed in the crude state.

(c) (±)-α-Cyano-3-phenoxybenzyl (−)-2(4-azidophenyl)-3-methylbutyrate 0.6 of pyridine in 10 ml of absolute toluene is added to a mixture of 1.6 g of the acid chloride obtained in (b) and 1.5 g of α-cyano-3-phenoxybenzyl alcohol in 20 ml of absolute toluene. The reaction mixture is stirred overnight at room temperature, then diluted with ether. The organic phase is washed with sodium bicarbonate solution, 2 N hydrochloric acid and brine, dried over Na$_2$SO$_4$, and concentrated. Chromatography on silica gel with toluene/ethyl acetate (10:1) as eluant yields the pure compound of the formula

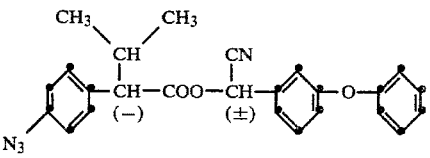

with a refractive index of n$_D^{20°}$=1.5775, an optical rotation $[\alpha]_D^{20°}$=+17° (CHCl$_3$, c=0.72) and a NMR spectrum (60 MHz, CDCl$_3$) of:

| | |
|---|---|
| 0.55–1.25 ppm | (m; 6H, 2CH$_3$) |
| 1.8–2.7 ppm | (m; 1H) |
| 3.25 ppm | (d; J = 10Hz; 1H) |
| 6.3–6.4 ppm | (2S; 1H) |
| 6.7–7.6 ppm | (m; 13H). |

EXAMPLE 2

Production of (±)-α-cyano-3-phenoxybenzyl (+)-2(4-azidophenyl)-3-methylbutyrate (a) (+)-2(4-Azidophenyl-3-methylbutyric acid The first mother liquor of the racemate cleavage in Example 1(a) is concentrated and the acid is liberated with dilute hydrochloric acid. After extraction with ethyl acetate, the organic extract is dried over Na$_2$SO$_4$ and concentrated. Then 23.3 g of this acid are dissolved at 60° C. in 330 ml of 63% alcohol and the solution is stirred into a solution of 15.6 g of (−)-phenylethylamine in 225 ml of 63% alcohol at 60° C. The reaction mixture is allowed to stand overnight at 30° C. to crystallise out and the precipitated salt (23 g) is collected by filtration. The precipitate is recrystallised once from 63% alcohol, affording 14 g of salt from which the desired (+)-2(4-azidophenyl)-3-methylbutyric acid is liberated in the manner described above and obtained pure by two recrystallisations.

Melting point: 95°–97° C.; $[\alpha]_D^{20°}$=+48° (CHCl$_3$, c=1.30).

(b) (−)-2(4-Azidophenyl)-3-methylbutyryl chloride 2 g of the acid obtained in (a) and 1.7 g of oxalyl chloride are heated to 60° C. in 35 ml of hexane. Then 1 drop of dimethyl formamide is added and the reaction mixture is stirred for 1 hour at 60° C. The cold solution is decanted and concentrated in a rotary evaporator. The resultant (+)-2(4-azidophenyl)-3-methylbutyryl chloride is further processed in the crude state.

(c) (+)-α-Cyano-3-phenoxybenzyl
(+)-2(4-azidophenyl)-3-methylbutyrate

To 2.1 g of the acid chloride obtained in (b) and 1.98 g of α-cyano-3-phenoxybenzyl alcohol in 20 ml of absolute toluene is added, at room temperature, 0.8 g of pyridine in 10 ml of absolute toluene. The reaction mixture is stirred overnight at room temperature, then diluted with ether. The organic phase is washed with sodium bicarbonate solution, 2 N hydrochloric acid and brine, dried over Na$_2$SO$_4$ and concentrated. Chromatography of the residue on silica gel with toluene/ethyl acetate (10:1) as eluant affords the pure compound of the formula

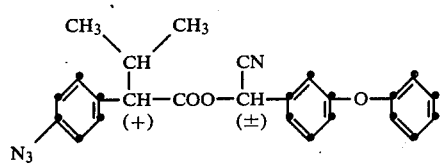

with a refractive index of n$_D^{22°}$=1.5785, an optical rotation [α]$_D^{20°}$=−17° (CHCl$_3$, c=0.64), and a NMR spectrum (60 MHz, CDCl$_3$) of:

| 0.5–1.2 ppm | (m; 6H, 2CH$_3$) |
| 1.85–2.65 ppm | (m; 1H) |
| 3.25 ppm | (d; J = 10Hz; 1H) |
| 6.3–6.4 ppm | (2S; 1H) |
| 6.65–7.7 ppm | (m; 13H). |

The following compounds are also obtained in analogous manner:

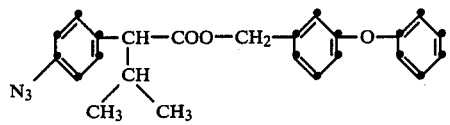

n$_D^{24,5°}$ : 1.5772

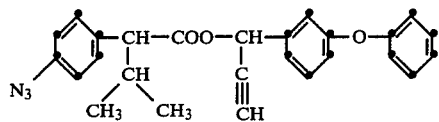

n$_D^{25°}$ : 1.5826

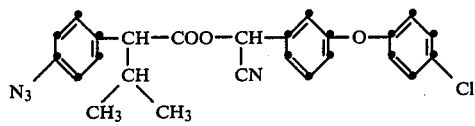

n$_D^{25°}$ : 1.5820

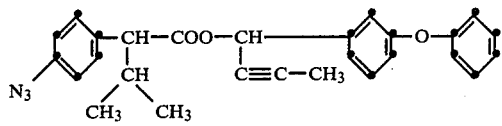

n$_D^{24,5°}$ : 1.5827

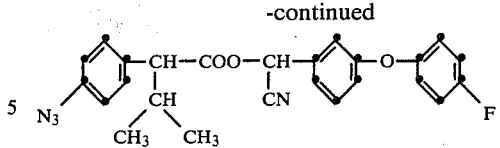

n$_D^{24,5°}$ : 1.5680

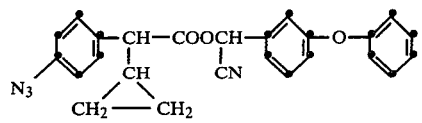

n$_D^{22,5°}$ = 1.5665

EXAMPLE 3

Insecticidal stomach poison action

Cotton plants were sprayed with a 0.05% aqueous emulsion of active ingredient. After the spray coating had dried, the cotton plants were populated with larvae of *Spodoptera littoralis* and *Heliothis virescens* in the L$_3$-stage. The test was carried out at 24° C. and 60% relative humidity.

In this test, the compounds of Examples 1 and 2 exhibited a good insecticidal stomach poison action against Spodoptera and Heliothis larvae.

EXAMPLE 4

Acaricidal action

Twelve hours before the test for acaricidal action, *Phaseolus vulgaris* plants were populated with an infested piece of leaf from a mass culture of *Tetranychus urticae*. The mobile stages which had migrated to the plants were sprayed with the emulsified test preparations from a chromatography atomiser such that the spray broth did not run off. A count of living and dead larvae, adults and eggs was made under a stereoscopic microscope after 2 and 7 days and the result expressed in percentage values. During the test run, the plants stood in greenhouse compartments at 25° C.

In this test, the compounds of Examples 1 and 2 were effective against adults, larvae and eggs of *Tetranychus urticae*.

EXAMPLE 5

(A) *Rhipicephalus bursa*

Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton-wool plug and placed on its head to enable the cotton wool to absorb the active substance emulsion. Evaluation of the action against adults was made after 2 weeks and of that against larvae after 2 days. Each test was repeated twice.

(B) *Boophilus microplus* (larvae)

Test were carried out with 20 OP-sensitive and 20 OP-resistant larvae using aqueous emulsions similar to those used in Test A. (The resistance refers to the tolerance towards diazinone). The compounds of Examples 1 and 2 were effective in these tests against adults and

What is claimed is:

1. A compound of the formula

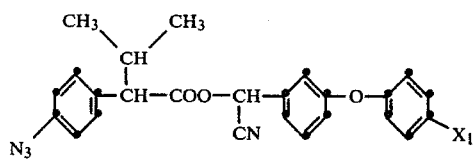

wherein $X_1$ is hydrogen, fluorine or chlorine.

2. A method for controlling insects and acarids which comprises applying to the locus thereof an insecticidally or acaricidally effective amount of a compound according to claim 1.

3. The compound according to claim 1 of the formula

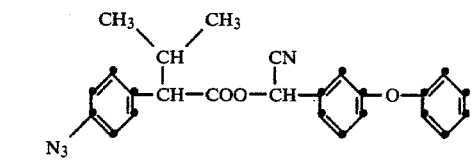

4. An insecticidal and acaricidal composition which contains, as active component an insecticidally or acaricadally effective amount of a compound according to claim 1, together with suitable carriers.

5. A compound of the formula

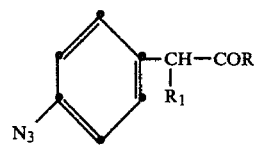

wherein $R_1$ is isopropyl or cyclopropyl, and R is hydroxyl, halogen or $C_1$-$C_4$alkoxy.

* * * * *